United States Patent [19]

Kelley

[11] Patent Number: 4,884,827

[45] Date of Patent: Dec. 5, 1989

[54] PARTIALLY TRANSPARENT LABEL

[75] Inventor: Thomas F. Kelley, Canton, Mass.

[73] Assignee: Norfolk Scientific Inc., Norwood, Mass.

[21] Appl. No.: 146,965

[22] Filed: Jan. 22, 1988

[51] Int. Cl.[4] .......... B42D 15/00; G09F 3/00; B32B 23/00; A61F 13/02

[52] U.S. Cl. .......... 283/81; 40/316; 156/DIG. 5; 428/40

[58] Field of Search .......... 283/81, 82, 101, 72; 40/316; 282/11.5 A, 9 A; 428/40; 156/DIG. 5

[56] References Cited

U.S. PATENT DOCUMENTS

| | | | |
|---|---|---|---|
| 2,069,609 | 2/1937 | Hanson | 283/81 |
| 2,532,011 | 11/1950 | Dahlquist et al. | 283/81 |
| 2,914,166 | 11/1959 | Bihler | 40/316 |
| 2,975,091 | 3/1961 | Tobey | 283/81 |
| 2,984,596 | 5/1961 | Franer | 283/81 |
| 3,228,129 | 1/1966 | Gwinn et al. | 283/81 |
| 4,312,523 | 1/1982 | Haines | 283/81 |
| 4,505,497 | 3/1985 | Katzman | 283/81 |
| 4,579,753 | 4/1986 | Breuers | 283/81 |

FOREIGN PATENT DOCUMENTS

| | | | |
|---|---|---|---|
| 755455 | 3/1967 | Canada | 156/DIG. 5 |

*Primary Examiner*—Douglas D. Watts
*Assistant Examiner*—Paul M. Heyrana, Sr.
*Attorney, Agent, or Firm*—Weingarten, Schurgin, Gagnebin & Hayes

[57] ABSTRACT

A plastic adhesive label for microsample collection tubes has opaque end portions for receipt of identifying markings, and a transparent middle portion to permit viewing of the contents of the collection tube. In use, the transparent portion of the label is wrapped around and adhered to a collection tube and the end portions of the label are brought together in adhesion, the end portions forming a flag which carries the identifying information. With the transparent portion of the label surrounding the collection tube, the contents of the tube are still visible to an observer for confirmation at the same time the identifying information is displayed on the label.

6 Claims, 1 Drawing Sheet

PARTIALLY TRANSPARENT LABEL

FIELD OF THE INVENTION

This invention relates to adhesive labels, and more particularly, to adhesive labels having transparent and opaque portions to facilitate viewing and labeling functions, respectively.

BACKGROUND OF THE INVENTION

A very wide variety of adhesive labels are commercially available. Most of these are general purpose labels, having an adhesive layer on one side and having their front surfaces adapted for written or typed identifications. Some are special purpose labels specifically configured for particular uses.

Despite this wide variety of known label types, there are apparently no labels specifically intended for identifying sample tubes having small diameters while simultaneously not obscuring the contents of such sample tubes from view.

A variety of blood collecting devices employ microsample collection tubes. It is necessary to label such tubes unambiguously and securely to provide positive identification from the time a blood sample is taken to the time the sample or the plasma therefrom is removed for analysis. Accordingly, it would be desirable to have a label which can be attached conveniently and securely to a microsample collection tube while not obscuring its contents.

SUMMARY OF THE INVENTION

The present invention provides a label for identifying sample collection tubes without obscuring their contents. This label is a strip of plastic having adhesive on one side, having the other side adapted to receive markings from a writing instrument such as a pen or pencil, and having a transparent band through its midsection.

In use, the transparent portion of the label is wrapped around a small diameter sample collection tube and the end portions are stuck to each other, resulting in a miniature flag carrying identifying information while simultaneously permitting the contents of the sample collection tube to be viewed.

DESCRIPTION OF THE DRAWING

The invention will be more fully understood from a consideration of the following detailed description taken in conjunction with the drawing, in which.

DETAILED DESCRIPTION

Figure 1:
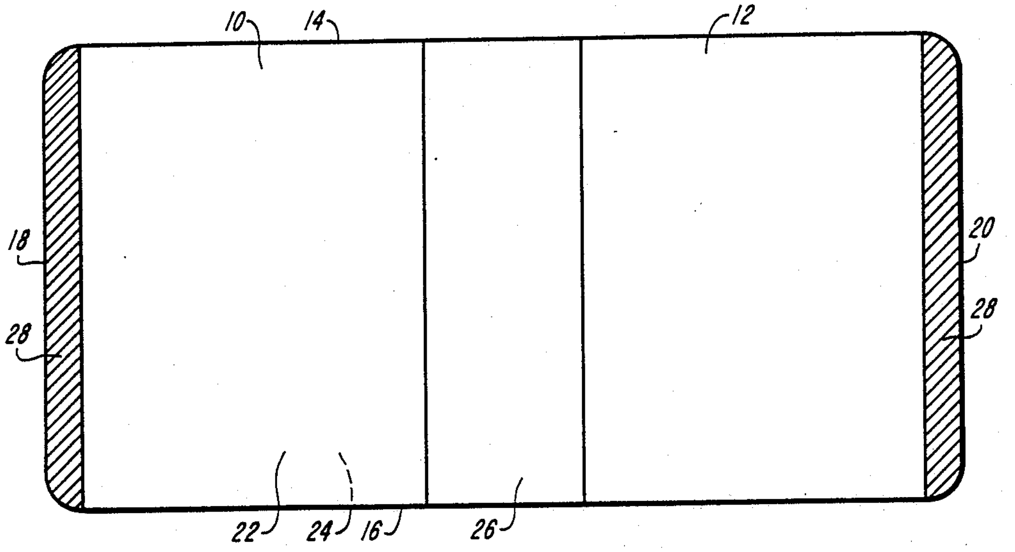
FIG. 1 shows a front view of the label of the invention.

As shown in FIG. 1, the invention is a label for identifying sample collection tubes, and other laboratory apparatus such as test tubes, syringes, pipet tips, etc., without obscuring their contents, and comprises a strip of plastic having first and second end portions 10 and 12 respectively, first and second substantially parallel edges 14 and 16 respectively, third and fourth substantially parallel edges 18 and 20 respectively which are themselves substantially perpendicular to first and second edges 14 and 16, a front surface 22, a rear surface 24, and a middle portion 26 which extends between the first and second edges 14 and 16.

Front surface 22 is adapted to receive markings from a writing instrument such as a pencil, a pen, or a laboratory marker. The rear surface 24 has a layer of adhesive material covering at least one end portion 10 or 12 and middle portion 26. This adhesive generally covers the entire rear surface 24.

Middle portion 26 is transparent, to permit ready viewing of the contents of a labeled tube. At least one of the end portions 10 and 12 is opaque to provide a contrasting background for the labeling information. Generally, both end portions are opaque. The end portions are generally lightly colored, and are preferably white. The opaque areas of the label have a surface which accepts markings from pen, pencil, "magic" laboratory markers, and other sorts of marking instruments.

In one embodiment of the invention, dark narrow bands 28 are located adjacent the third and fourth edges 18 and 20, to aid in removing the label from the backing sheet by making it more visible, and to aid in attaching the labels to the sample collection tubes to be identified, as will be made clear below.

The labels of the invention are readily manufactured by well-established techniques known to those skilled in the art. Suitable plastics for use in the inventive labels are such materials as poly(vinyl chloride), polyethylene, polypropylene, and polyesters such as mylar. The sheets of plastic from which the labels are made are generally 0.001–0.01 inches thick, preferably between 0.002 and 0.005 inches in thickness.

Adhesives suitable for use in the inventive labels are those known in the trade as permanent pressure-sensitive adhesives and which are also compatible with most plastics such as polyethylene, polypropylene, teflon, styrene, and ABS. Adhesives meeting these criteria will also bond to other materials such as metal and glass.

The labels are produced by any suitable technique known to the art, such as, for example, by applying a layer of adhesive to one side of a sheet of clear or frosty plastic, adhering the sheet to a backing sheet from which it can be removed, printing white areas intended to be end portions of the labels adapted to accept writing, and printing black stripes on desired sections of the end portions, this step being an optional operation to provide an aid for bringing the label ends together. The final steps involve die-cutting the labels from the sheet and stripping away excess plastic, leaving labels attached to a backing sheet.

Figure 2:
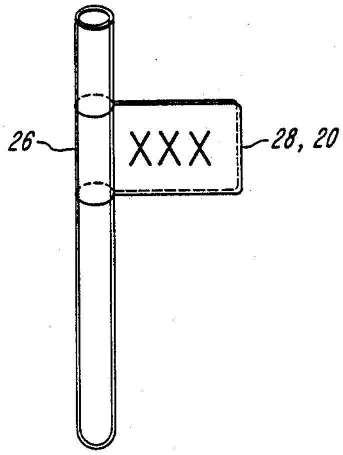
FIG. 2 shows an enlarged view of the label of the invention attached to a microsample collection tube.

Various methods of use are possible. In one, the label is commonly marked with an identifying name, number, or symbol on the front surface 22 of one or both of the end portions 10 and 12. Generally marking is done before the label is removed from its backing sheet but may be done after wrapping of the label around the tube. The label is next removed from the backing sheet and the transparent middle portion 26 is wrapped around a microsample collection tube to be labeled, third and fourth edges 18 and 20 are brought together, proper alignment being assisted by dark bands 28, and the rear surfaces of end portions 10 and 12 are brought into contact, thus giving rise to a flag attached to the sample collection tube, as shown in FIG. 2. The dark bands 28 assure that the ends will be brought together exactly, leaving no portion of exposed adhesive, and thus permitting the flag to be "furled" about the tube for insertion into a centrifuge head, and "unfurled" easily without sticking to itself. As the transparent middle portion 26 of the label is wrapped around the tube, the contents of the tube are visible through the label and are not obscured.

The label thus attached to the sample collection tube being identified serves not only as the identifying label, but also serves as a handle for the tube, facilitating subsequent laboratory operations.

Other embodiments of the invention will be apparent to those skilled in the art from a consideration of this specification or practice of the invention disclosed herein. It is intended that the specification and example be considered as exemplary only, with the true scope and spirit of the invention being indicated by the following claims.

What is claimed is:

1. A label for identifying sample collection tubes without obscuring their contents, comprising:
   - a strip of plastic having first and second end portions, first and second substantially parallel edges, third and fourth substantially parallel edges which are substantially perpendicular to said first and second edges, a front surface, a rear surface, and a middle portion extending between said first and second edges and separating said first and second end portions,
   - said front surface being capable of receiving markings from a writing instrument on both of said end portions,
   - said rear surface having an adhesive material on at least one of said end portions and on said middle portion,

- said middle portion being transparent,
   - each of said end portions being opaque, and having a dark band thereon adjacent said third and fourth edges respectively, to facilitate alignment of the ends of the label with each other.

2. The label of claim 1 wherein said end portions are light colored.

3. The label of claim 2 wherein said end portions are white.

4. The label of claim 1 wherein the adhesive material covers the rear surface of the label.

5. The label of claim 1 wherein said first and second edges are longer than said third and fourth edges.

6. A marking tag for small liquid handling tube, comprising:
   - a flexible strip having a transparent middle portion and two opaque end portions, said middle portion being located between said end portions and adjacent thereto;
   - both end portions of said strip having markable surfaces to permit writing of information;
   - said strip being at least partially coated with an adhesive on a side opposite to said markable portions, said adhesive being located on at least said middle portion and on one end portion, thereby permitting said strip to be adherently wrapped around said tube, with said transparent portion aligned with the tube to permit viewing of the tube contents, and with the writing portions extending away from said tube.

* * * * *